United States Patent [19]

Carn

[11] Patent Number: 5,662,657
[45] Date of Patent: Sep. 2, 1997

[54] INTRAMEDULLARY BONE PLUG

[75] Inventor: Ronald M. Carn, Redding, Calif.

[73] Assignee: SunMed, Inc., Redding, Calif.

[21] Appl. No.: 587,491

[22] Filed: Jan. 17, 1996

[51] Int. Cl.$^6$ ........................................... A61F 2/28
[52] U.S. Cl. ............................. 606/95; 606/92; 606/99
[58] Field of Search .......................... 606/92, 93, 94, 606/95, 99, 72

[56] References Cited

U.S. PATENT DOCUMENTS

| | | |
|---|---|---|
| 4,175,555 | 11/1979 | Herbert . |
| 4,245,359 | 1/1981 | Stuhmer . |
| 4,276,659 | 7/1981 | Hardinge . |
| 4,293,962 | 10/1981 | Fuson . |
| 4,302,855 | 12/1981 | Swanson . |
| 4,344,190 | 8/1982 | Lee et al. . |
| 4,447,915 | 5/1984 | Weber . |
| 4,523,587 | 6/1985 | Frey . |
| 4,670,915 | 6/1987 | Freeman . |
| 4,686,973 | 8/1987 | Frisch . |
| 4,745,914 | 5/1988 | Frey et al. . |
| 5,078,746 | 1/1992 | Garner . |
| 5,092,891 | 3/1992 | Kummer et al. . |
| 5,100,405 | 3/1992 | McLaren . |
| 5,192,283 | 3/1993 | Ling et al. . |
| 5,192,303 | 3/1993 | Gatturna et al. ................... 606/72 |
| 5,197,989 | 3/1993 | Hinckfuss et al. . |
| 5,290,318 | 3/1994 | Ling et al. . |
| 5,340,362 | 8/1994 | Carbone . |
| 5,376,120 | 12/1994 | Sarver et al. . |
| 5,383,932 | 1/1995 | Wilson et al. . |
| 5,403,136 | 4/1995 | Mathys . |
| 5,927,421 | 5/1990 | Goble et al. . |

FOREIGN PATENT DOCUMENTS

| | | | |
|---|---|---|---|
| 6408 | 6/1978 | European Pat. Off. | .................. 606/95 |
| 434-604-A | 11/1990 | European Pat. Off. . | |
| 4136317-A1 | 5/1993 | Germany . | |
| 2211741 | 7/1989 | United Kingdom | .................... 606/95 |

OTHER PUBLICATIONS

Wright Mfg. Co, Journal of Bone & Joint Surgery, Jul. 1954, p. 27.

*Primary Examiner*—Michael Buiz
*Assistant Examiner*—Julian W. Woo
*Attorney, Agent, or Firm*—Kelly Bauersfeld Lowry & Kelly, LLP

[57] ABSTRACT

A bone plug is provided for insertion into the medullary canal of a patient bone during orthopedic surgery, wherein the bone plug restricts or prevents passage of bone cement introduced under pressure into the medullary canal. The bone plug comprises a generally cylindrical member formed from a biocompatible material such as polyethylene and having sets of distal and proximal fins formed thereon. The bone plug is installed with an insertion tool that can be readily manipulated to orient the distal fins to define distally presented outer edges to anchor the bone plug by biting into patient bone, whereas the proximal fins are oriented to define proximally presented outer edges to seal against bypass flow of bone cement past the bone plug.

17 Claims, 3 Drawing Sheets

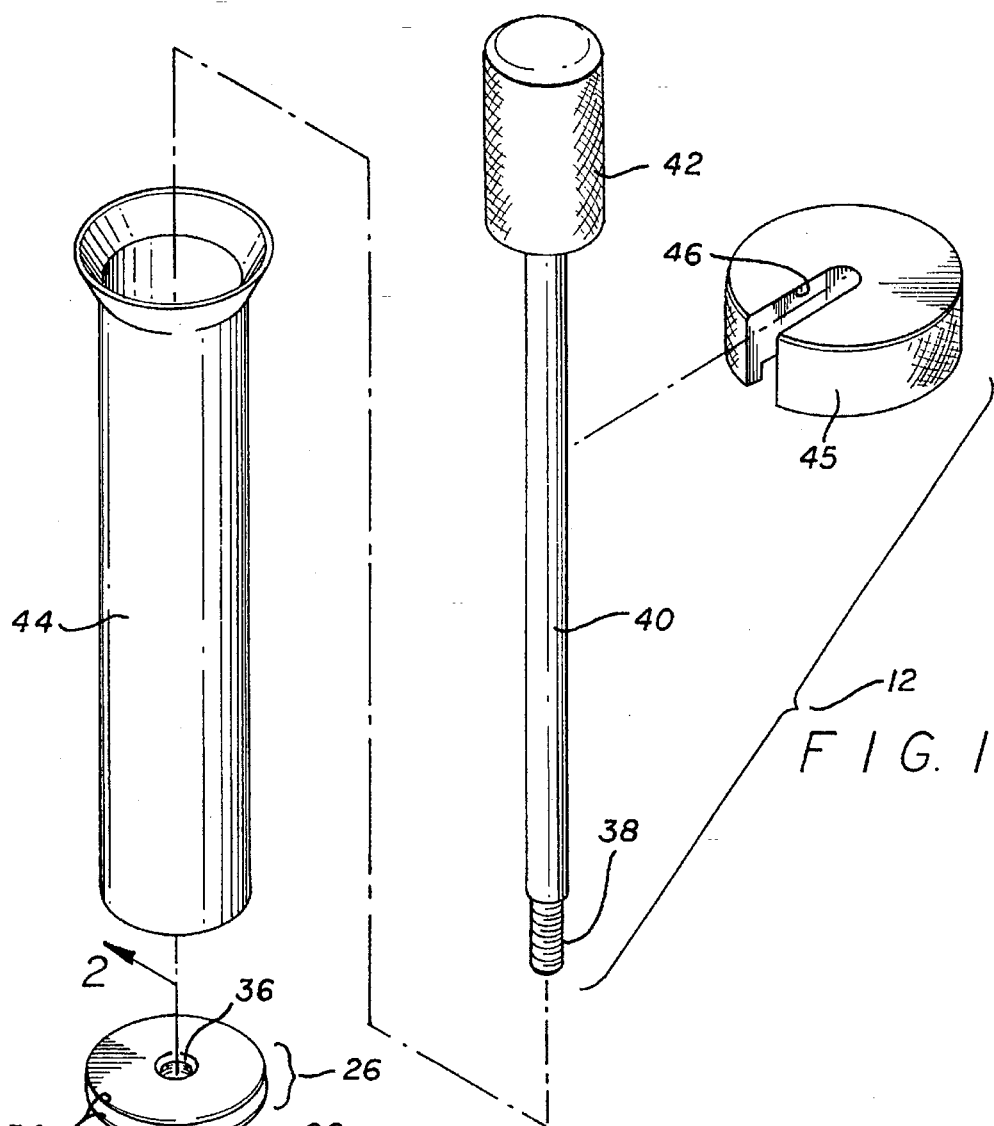
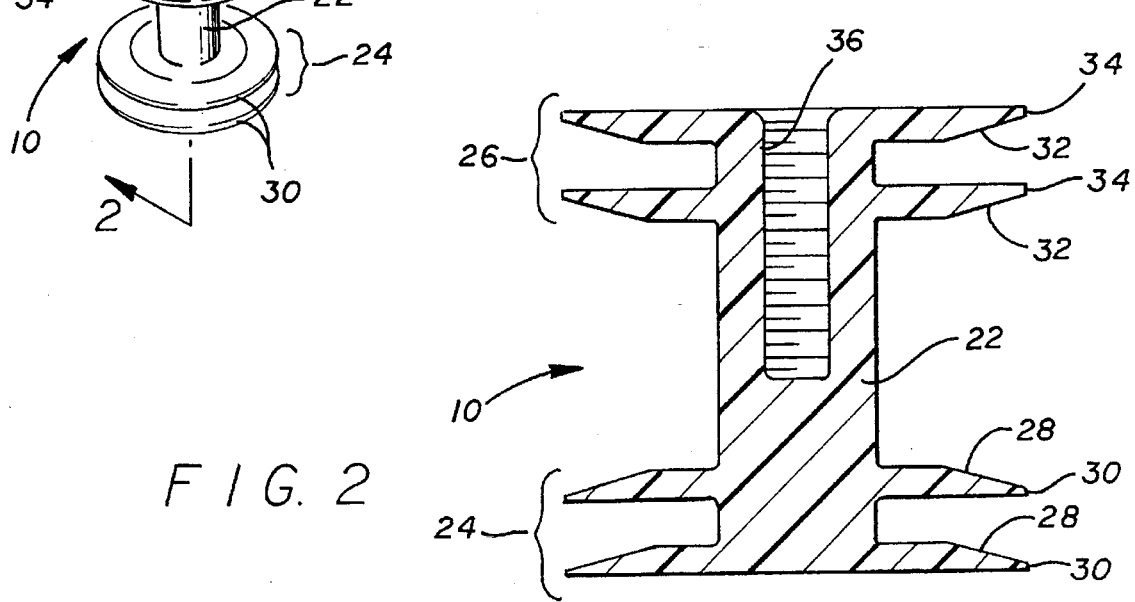

INTRAMEDULLARY BONE PLUG

BACKGROUND OF THE INVENTION

This invention relates generally to improvements in devices and procedures for artificial joint replacement (arthroplasty). More specifically, this invention relates to an improved intramedullary bone plug for confining or restricting the placement of bone cement introduced under pressure into the medullary canal of a patient bone during arthroplasty surgery, such as a hip joint replacement.

Artificial or prosthetic joint structures are used extensively to repair or replace a patient joint, particularly such as hip, knee and shoulder joints. The prosthesis typically comprises a biocompatible structure or structures formed from cobalt-chrome alloy with a size and shape for secure affixation to a surgically resected patient bone. In many cases, the prosthetic device includes an elongated stem for slide-fit placement into the exposed medullary canal of a resected patient bone, such as the upper end of a patient's femur in the case of a hip replacement. A bone cement, typically methyl methacrylate, is often introduced under pressure into the medullary canal to provide a positive and stable prosthesis attachment to the patient bone. The pressurized bone cement is intended to fill the interstices of the bone structure in surrounding relation to the prosthetic device to result in optimal prosthesis fixation.

When pressurized bone cement is introduced into the medullary canal, it is necessary or desirable to use a restrictor or plug element to confine the cement to surrounding relation with the prosthesis, rather than to permit the bone cement to travel distally through the medullary canal in a direction away from the prosthesis. In this regard, numerous restrictor or plug devices have been developed for this purpose, and are adapted to be installed into the medullary canal immediately prior to placement of the prosthesis and bone cement. However, such prior restrictor or plug devices have not functioned in a fully satisfactory manner. To the contrary, such prior restrictor or plug devices have suffered from bypass leakage of the bone cement, or alternately from undesired sliding movement in a distal direction when subjected to bone cement under pressure. Either problem results in inadequate pressurization of the cement and corresponding less-than-optional fixation of the prosthesis.

There exists, therefore, a significant need for an improved bone plug for use in orthopedic surgery, wherein the bone plug is securely anchored within the medullary canal and further provides a high quality seal to prevent bypass leakage of cement. The present invention fulfills these needs and provides further related advantages.

SUMMARY OF THE INVENTION

In accordance with the invention, an improved intramedullary bone plug is provided for controlling the placement of pressurized bone cement into the medullary canal of a patient bone during orthopedic surgery such as hip replacement surgery. The improved bone plug includes a generally cylindrical body in combination with distal fins and proximal fins which function respectively to anchor the plug within the patient bone and to prevent bypass leakage of pressurized bone cement in a distal direction past the plug.

The improved bone plug is formed from a biocompatible material such as polyethylene or the like and preferably as a one-piece construction to include a pair of axially spaced distal fins and a corresponding pair of axially spaced proximal fins. The distal fins, conveniently include tapered side walls on the proximal sides thereof to facilitate flexing in a downstream or distal direction. Conversely, the proximal fins desirably include tapered side walls at the distal sides thereof to facilitate flexing in an upstream or proximal direction.

The insertion tool comprises an elongated stylet with a threaded tip at a distal end thereof for thread-in reception into a threaded socket formed in the proximal end of the plug body. The stylet supports the bone plug for slide-fit insertion into a retainer sleeve. In use, the bone plug is slidably fitted into a proximal or aft end of the retainer sleeve, and then advanced sufficiently to move the distal fins past a forward or distal sleeve end. During initial placement of the plug into the insertion tool, the distal and proximal fins flex within the retainer sleeve to orient the outer fin edges in a proximally presented direction. However, movement of the distal fins beyond the retainer sleeve distal end allows the distal fins to re-orient radially. The bone plug is then retracted back into the retainer sleeve, resulting in reorientation of the distal fins with the outer edges thereof presented distally.

In this orientation, the bone plug of the present orientation is installed into the medullary canal with the insertion tool, including the stylet and the retainer sleeve. When the desired plug position is achieved, the insertion tool is removed, whereby the distal fins anchor the plug while the proximal fins seal against bypass leakage of bone cement. The bone plug of this insertion is particularly suited for insertion into a patient bone having a canal size that increases in a direction away from the proximal end of the resected bone.

Other features and advantages of the improved intramedullary bone plug of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is an exploded perspective view showing the improved bone plug and related insertion tool embodying the novel features of the invention;

FIG. 2 is a sectional view of the bone plug, taken generally on the line 2—2 of FIG. 1;

DETAILED DESCRIPTION OF THE PREFERRED EMBODIMENT

Figure 3:
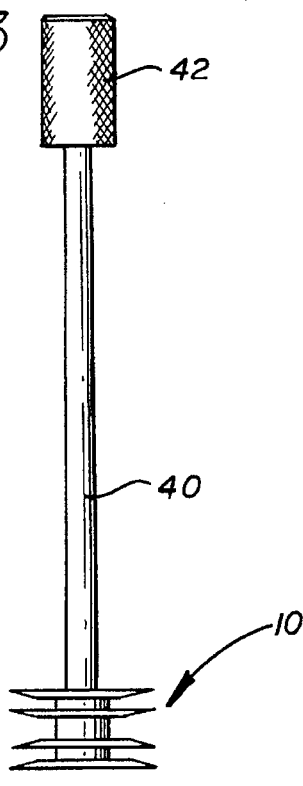
FIG. 3 is an elevational view showing attachment of the bone plug to a portion of the insertion tool.

As shown in the exemplary drawings, an improved intramedullary bone plug is referred to generally by the reference numeral 10. The bone plug 10 is designed for placement into the medullary canal of a patient bone, by means of an insertion tool 12.

As shown best in FIGS. 7–10, the bone plug 10 of the present invention is positioned within the medullary canal 14 of a patient bone, such as a resected femur 16 in the case of hip replacement surgery, at a location spaced slightly downstream or distally from an associated prosthesis 18. In use, the bone plug 10 provides a barrier to block and retain bone cement 20 introduced under pressure into the medullary canal 14. The bone plug 10 thus confines the bone cement 20 to the space surrounding the prosthesis 18, to achieve substantially optimum prosthesis fixation.

The bone plug 10 is formed from a suitable biocampatible material such as polyethylene or the like, and preferably is a one-piece component. The plug 10 comprises a generally cylindrical body 22 (FIGS. 1 and 2), in combination with a set of distally positioned fins 24 and another set of proximally positioned fins 26. The diametric size of the plug body 22 with the sets of fins 24, 26 is chosen to fit into the medullary canal 14, with the fins 24, 26 engaging the patient bone lining the canal as will be described in more detail. In this regard, the bone plug 10 of the present invention is particularly suited to fit into a medullary canal of a diametric size which increases in a direction away from the proximal or resected end of the patient bone. For the construction and functional operation of a related bone plug configured for use with a medullary canal of approximately uniform cross sectional size, see copending U.S. Ser. No. 08/607,242.

The distal fins 24 are formed as a pair of axially spaced annular rings at the downstream or distal end of the plug body 22. As shown best in FIG. 2, this pair of distal fins 24 include tapered proximal side faces 28 to facilitate fin flexing in a distal direction, as will be described, to orient the radial outer edges 30 of the distal fins in a distally presented direction.

The proximal fins 26 are also formed as a pair of axially spaced annular rings located at the upstream or proximal end of the plug body. These proximal fins 26 have tapered distal side faces 32 to facilitate fin flexing in a proximal direction to orient the radial outer edges 34 thereof in a proximally presented direction.

The plug body 22 further includes a threaded socket 36 formed therein at the proximal end thereof. The threaded socket 36 is adapted for thread-in connection with a threaded tip 38 on an elongated stylet 40 forming a portion of the installation tool 12. The elongated stylet 40 is provided to manipulate and position the bone plug into the medullary bone canal, and conveniently includes an enlarged handle 42 at a rear end thereof to faciliate manual handling.

Figure 4:
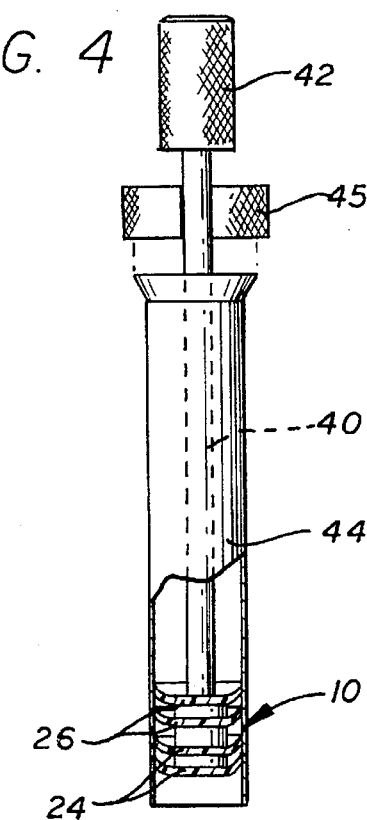
FIG. 4 is an elevational view, shown partly in vertical section, illustrating slide-fit placement of the bone plug into a retainer sleeve forming part of the insertion tool.
Figure 5:
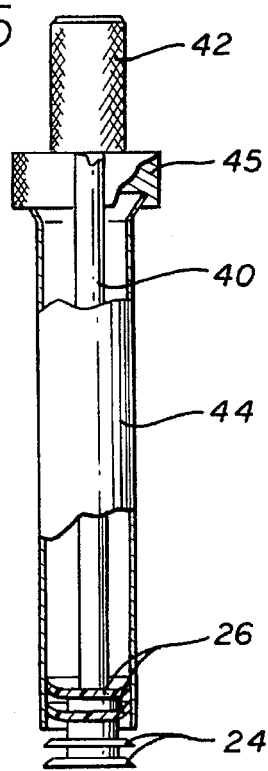
FIG. 5 is an elevational view similar to FIG. 4, and showing movement of the bone plug to position distal fins thereon beyond a distal end of the retainer sleeve.
Figure 6:
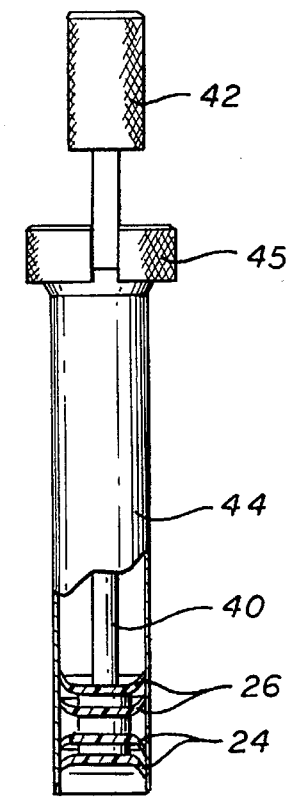
FIG. 6 is another elevational view similar to FIG. 4, and showing retraction of the bone plug and distal fins thereon back into the retainer sleeve.

As shown in FIGS. 3 and 4, the elongated stylet 40 is threadably attached to the plug body 22, whereupon the bone plug is slidably fitted into a hollow cylindrical retainer sleeve 44 which also forms part of the installation tool. During this initial slide-fit placement, both the distal and proximal fins 24, 26 have their outer edges 30, 34 flexed proximally. Importantly, however, the bone plug 10 is advanced within the sleeve 44 using the stylet 40 to position the distal fins 24 beyond the associated distal end of the retainer sleeve, as viewed in FIG. 5. A spacer disk 45 removably placed over the stylet 40 between the handle 42 and a rear end of the retainer sleeve 44 provides a stop indicative of distal fin movement beyond the distal end of the sleeve 44. The bone plug is then retracted to withdraw the distal fins 24 back into the retainer sleeve 44 (FIG. 6), resulting in the outer edges 30 of the distal fins 24 being flexed in a distally presented direction. Accordingly, as shown in FIG. 6, the bone plug 10 is positioned within the retainer sleeve 44 with the distal fins 24 flexed distally and with the proximal fins 26 flexed proximally.

Figure 7:
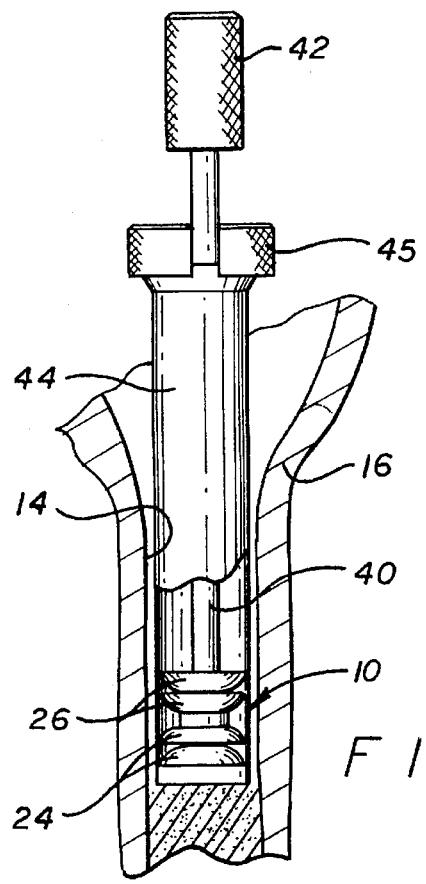
FIG. 7 is an elevational view, shown partly in vertical section, depicting initial placement of the bone plug onto the medullary canal of a resected femur during hip replacement surgery.
Figure 8:
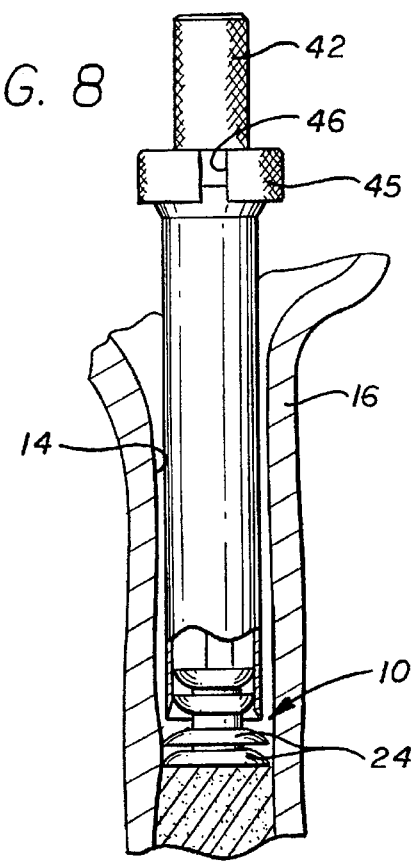
FIG. 8 is another elevational view similar to FIG. 7, and showing initial placement of the distal fins in engagement with patient bone.
Figure 9:
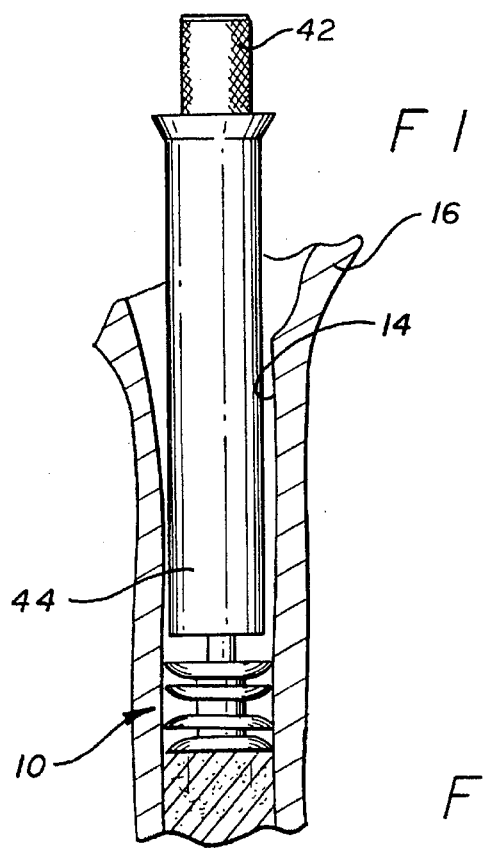
FIG. 9 is a further elevational view similar to FIG. 7 to show further withdrawal of the insertion tool.
Figure 10:
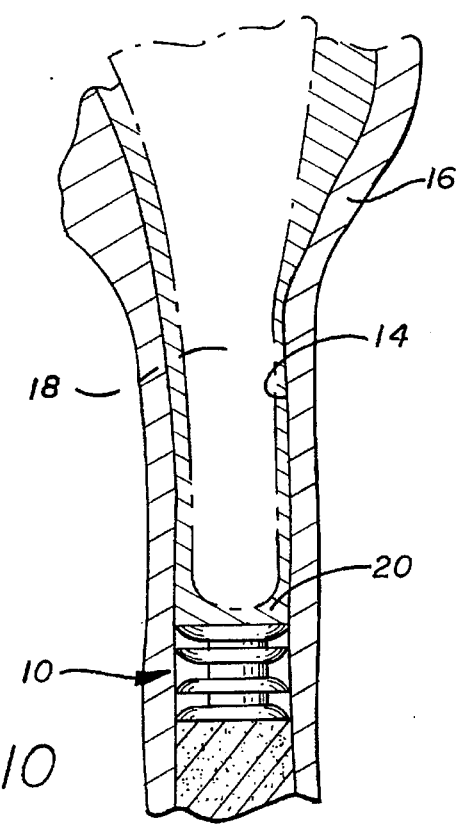
FIG. 10 is an elevational view, shown partly in vertical section, to illustrate the bone plug in relation to an installed hip prosthesis.

FIG. 7 shows use of the thus-assembled installation tool 12 to place the bone plug 10 into the medullary canal 14 of a resected femur 16. As shown, the stem 40 and sleeve 44 are used to position the bone plug at a desired depth within the medullary canal 14, at which time the stylet 40 is advanced as viewed in FIG. 8 so that the handle 42 seats on the spacer disk 45. This motion displaces the distal fins 24 to a position with the outer edges biting into the patient bone. The spacer disk 45 is then laterally separated from the stylet 40, by means of an open slot 46 in the disk 45, to permit sufficient retraction of the retainer sleeve 44 to place the proximal fins 26 (FIG. 9) in engagement with patient bone. The entire installation tool 12 is then carefully separated from the bone plug 10, leaving the bone plug in position (FIG. 10) with the distally turned edges 30 of the distal fins 24 engaging and biting into the adjacent patient bone to firmly secure the plug in the medullary canal. The proximal fins 26 have their outer edges 34 turned proximally to engage the bone and thereby serve as effective seals to prevent bypass leakage of bone cement 16 introduced under pressure into the medullary canal.

A variety of further modifications and improvements to the bone plug 10 of the present invention will be apparent to those skilled in the art. Accordingly, no limitation on the invention is intended by way of the foregoing description and accompanying drawings, except as set forth in the appended claims.

What is claimed is:

1. An intramedullary bone plug and installation tool therefor, comprising, in combination:

a generally cylindrical plug body having a size and shape for slide-fit reception into the medullary canal of a patient bone;

at least one flexible distal fin on said plug body and extending radially outwardly therefrom, said at least one distal fin defining a distally turned outer edge when positioned within the medullary canal;

at least one flexible proximal fin on said plug body and extending radially outwardly therefrom, said at least one proximal fin defining a proximally turned outer edge when positioned within the medullary canal; and an installation tool including a retainer sleeve for slide-fit reception of said bone plug with said at least one distal fin having its outer edge turned distally and with said at least one proximal fin having its outer edge turned proximally, said retainer sleeve defining a bore with a cross sectional size at least slightly less than the diametric size of said distal and proximal fins;

said plug body being slidably inserted into said retainer sleeve with said distal and proximal fins having the outer edges thereof turned proximally upon engagement with the interior of said retainer sleeve, said plug body being advanced through said retainer sleeve to position said distal fin axially beyond a distal end of said retainer sleeve, and then retracted back into said retainer sleeve whereby said outer edge of said distal fin is re-oriented in a distally presented direction.

2. The intramedullary bone plug of claim 1 wherein said plug body is formed integrally with said at least one distal and proximal fins.

3. The intramedullary bone plug of claim 2 wherein said bone plug is formed from a biocompatible plastic material.

4. The intramedullary bone plug of claim 2 wherein said at least one distal fin comprises an axially spaced pair of distal fins.

5. The intramedullary bone plug of claim 4 wherein said at least one proximal fin comprises an axially spaced pair of proximal fins.

6. The intramedullary bone plug of claim 1 wherein said at least one proximal fin comprises an axially spaced pair of proximal fins.

7. The intramedullary bone plug of claim 1 wherein said plug body has a proximal end with a threaded socket formed therein.

8. The intramedullary bone plug of claim 7 further including the installation tool comprising an elongated stylet having a threaded tip for thread-in engagement with said threaded socket.

9. The intramedullary bone plug of claim 8 wherein said installation tool further includes spacer means for maintaining said elongated stylet and said retainer sleeve in predetermined relation to each other.

10. An intramedullary bone plug and installation tool therefor, comprising, in combination:

a generally cylindrical plug body having at least one radially outwardly projecting flexible distal fin and at least one radially outwardly projecting flexible proximal fin thereon; and an installation tool having an elongated stylet with a distal tip including means for removable connection to a proximal end of said plug body, and a retainer sleeve for slide-fit mounting on said elongated stylet and for slide-fit reception of said plug body, said retainer sleeve defining a bore with a cross sectional size at least slightly less than the diametric size of said distal and proximal fins;

said plug body being slidably inserted with said elongated stem into said retainer sleeve whereby said distal and proximal fins have outer edges thereof turned proximally upon engagement with the interior of said retainer sleeve;

said plug body being advanced through said retainer sleeve to position said distal fin axially beyond a distal end of said sleeve, and then retracted back into said retainer sleeve whereby said outer edge of said distal fin is re-oriented in a distally presented direction;

said installation tool being insertable into the medullary canal of a resected patient bone, and said retainer sleeve and installation tool being separated from said bone plug to leave said bone plug within the medullary canal with said distal and proximal fins having their outer edges respectively turned distally and proximally.

11. The combination of claim 10 wherein said plug body is formed integrally with said at least one distal proximal fins.

12. The combination of claim 11 wherein said bone plug is formed from a biocompatible plastic material.

13. The combination of claim 10 wherein said at least one distal fin comprises an axially spaced pair of distal fins.

14. The combination of claim 13 wherein said at least one proximal fin comprises an axially spaced pair of proximal fins.

15. The combination of claim 10 wherein said plug body has a proximal end with a threaded socket formed therein.

16. The combination of claim 10 wherein said elongated stylet has a proximal end with a handle thereon, said installation tool further including a spacer disk for mounting between said handle and a proximal end of said retainer sleeve to maintain a predetermined spacing therebetween, said spacer disk being laterally removable from said elongated stylet.

17. A method of placing a bone plug into the medullary canal of a resected patient bone, said bone plug comprising a generally cylindrical plug body having at least one radially outwardly projecting distal fin and at least one radially outwardly projecting proximal fin formed thereon, said method comprising the steps of:

slidably fitting the bone plug into the proximal end of a retainer sleeve having an internal bore sized so that outer edges of the distal and proximal fins are turned proximally within the sleeve;

advancing the bone plug through the retainer sleeve to expose the distal fin at a distal end of the sleeve while retaining the proximal fin within the sleeve;

retracting the bone plug back into the retainer sleeve so that the distal fin has its outer edge turned distally within the sleeve;

slidably fitting the retainer sleeve with the bone plug thereon into the medullary canal of the resected patient bone; and slidably withdrawing the retainer sleeve from the bone to leave the bone plug within the medullary canal with its distal fin turned distally and its proximal fin turned proximally.

* * * * *